(12) United States Patent
Restrepo et al.

(10) Patent No.: US 8,298,590 B2
(45) Date of Patent: Oct. 30, 2012

(54) METHOD FOR EXTRACTION OF MATERIAL FROM A SAPINDACEA FAMILY FRUIT

(76) Inventors: Jaime Toro Restrepo, Medellin (CO); James Alberto Jimenez Martinez, Medellin (CO); Luis Fernando Echeverri Lopez, Medellin (CO); Sandra Patricia Zapata Porras, Medellin (CO)

( * ) Notice: Subject to any disclaimer, the term of this patent is extended or adjusted under 35 U.S.C. 154(b) by 0 days.

(21) Appl. No.: 12/776,511

(22) Filed: May 10, 2010

(65) Prior Publication Data

US 2011/0274777 A1    Nov. 10, 2011

(51) Int. Cl.
*A61K 36/00*    (2006.01)
(52) U.S. Cl. .......................................... 424/725; 424/777
(58) Field of Classification Search .................. None
See application file for complete search history.

(56) References Cited

U.S. PATENT DOCUMENTS

2010/0291241 A1 * 11/2010 Restrepo et al. .............. 424/725

FOREIGN PATENT DOCUMENTS

CN    101069544 A  * 11/2007

OTHER PUBLICATIONS

Tsuzuki et al, Antifungal activity of the extracts and saponins from *Sapindus saponaria* L., Anais da Academia Brasileira de Ciencias (2007) vol. 79, No. 4, pp. 557-583.*
Alvarez et al, Controlling powdery mildew of roses using a plant extract and foliar fertilizers, 2001 APS/MSA/SON joint meeting MSA abstracts of presentations, 91 (6), 2001.*

* cited by examiner

*Primary Examiner* — Qiuwen Mi
(74) *Attorney, Agent, or Firm* — John J Martinez; Martinez Patents P.C.

(57) ABSTRACT

The invention of the present application provides a standardized method to obtain a material from Sapindacea family fruits, wherein the material is utilized by itself or in combination with other compounds to make preparations. The material by itself has surfactant, emulsifying and foaming properties, among others. In addition, the invention provides a preparation wherein the material is used in combination with *Swinglea glutinosa* extract. The preparation enhances the ability of the *Swinglea glutinosa* extract to kill and prevent fungi, and to kill and repel insects and mites.

7 Claims, No Drawings

METHOD FOR EXTRACTION OF MATERIAL FROM A SAPINDACEA FAMILY FRUIT

BACKGROUND OF THE INVENTION

1. Area of the Invention

The present invention is related to how to obtain material from a Sapindacea family fruit, and uses of the material alone or combined in preparations with other compounds. In previous pending unpublished U.S. patent application Ser. No. 12/466,801, which is incorporated herein in its entirety by reference, the same inventors of the present application described an extract that is used in combination with the Sapindacea family fruit derived material to make a preparation, wherein the preparation is described herein.

2. Description of Prior Art

Sapindacea family fruit derived materials had been described to have beneficial uses.

For example, Kumar Arora S. et al. in U.S. Publication No. 2005/0249831 A1 discloses an extract from *Sapindus trifoliatus* that is used as a treatment for migraine.

Kusano H. et al. in U.S. Publication No. 2007/0140984 A1 also mentions that components derived from *Sapindus mukurossi* plants have antibacterial effects.

Unfortunately, there is no description in the prior art of a standardized method to obtain a good yield of a Sapindacea family fruit derived material that can be utilized by itself or in combination to make preparations from which further beneficial uses can be attained. The Invention of the present Application overcomes these prior art limitations.

SUMMARY OF THE INVENTION

The invention of the present application provides a standardized method to obtain a material from Sapindacea family fruits, wherein the material is utilized by itself or in combination with other compounds to make preparations. The material by itself has surfactant, emulsifying and foaming properties, among others. In addition, the invention provides a preparation wherein the material is used in combination with *Swinglea glutinosa* extract. The preparation enhances the ability of the *Swinglea glutinosa* extract to kill fungi, and to kill and repel insects and mites.

More specifically, the invention of the present application provides a method to extract a material from the Sapindaceae family fruit, wherein the method comprises:
- A. Obtaining a Sapindaceae family fruit, wherein the Sapindaceae family fruit is brownish gold, and wherein said Sapindaceae family fruit skin shows wrinkles;
- B. Breaking the Sapindaceae family fruit skin and pulp without breaking the Sapindaceae family fruit seed;
- C. Exposing the broken Sapindaceae family fruit skin and pulp and the unbroken Sapindaceae family fruit seed to a solvent;
- D. Separating all solid particles from the mix of broken Sapindaceae family fruit skin and pulp, the unbroken Sapindaceae family fruit seed, and the solvent, wherein a liquid portion remains;
- E. Retiring the solvent from the liquid portion, wherein the liquid portion without the solvent constitutes the material.

In one aspect of the method of the present invention, the mix of the broken Sapindaceae family fruit skin and pulp, the unbroken Sapindaceae family fruit seed, and the solvent is exposed to activated carbon before separating all solid particles.

In another aspect of the method of the present invention, the Sapindaceae family fruit is the *Sapindus saponaria* fruit.

In one more aspect of the method of the present invention, the solvent amount is at least one part per one part of the total initial weight of the skin plus the pulp plus the seed.

The present invention also provides a material derived from a Sapindaceae family fruit, wherein the material is derived from the Sapindaceae family fruit by a method comprising:
- A. Obtaining a Sapindaceae family fruit, wherein the Sapindaceae family fruit is brownish gold, and wherein said Sapindaceae family fruit skin shows wrinkles;
- B. Breaking the Sapindaceae family fruit skin and pulp without breaking the Sapindaceae family fruit seed;
- C. Exposing the broken Sapindaceae family fruit skin and pulp and the unbroken Sapindaceae family fruit seed to a solvent;
- D. Separating all solid particles from the mix of broken Sapindaceae family fruit skin and pulp, the unbroken Sapindaceae family fruit seed, and the solvent, wherein a liquid portion remains;
- E. Retiring the solvent from the liquid portion, wherein the liquid portion without the solvent constitutes the material.

In one aspect of the material of the present invention, the mix of broken Sapindaceae family fruit skin and pulp, the unbroken Sapindaceae family fruit seed, and the solvent is exposed to activated carbon before separating all solid particles.

In another aspect of the material of the present invention, the Sapindaceae family fruit is the *Sapindus saponaria* fruit.

In one more aspect of the material of the present invention, the solvent amount is at least one part per one part of the total initial weight of the skin plus the pulp plus the seed.

Furthermore, the present invention provides a preparation that comprises an extract from *Swinglea glutinosa* and a material derived from a Sapindaceae family fruit.

In one main aspect of the preparation of the present invention, the material is derived from the Sapindaceae family fruit by a method comprising:
- A. Obtaining a Sapindaceae family fruit, wherein the Sapindaceae family fruit is brownish gold, and wherein said Sapindaceae family fruit skin shows wrinkles;
- B. Breaking the Sapindaceae family fruit skin and pulp without breaking the Sapindaceae family fruit seed;
- C. Exposing the broken Sapindaceae family fruit skin and pulp and the unbroken Sapindaceae family fruit seed to a solvent;
- D. Separating all solid particles from the mix of broken Sapindaceae family fruit skin and pulp, the unbroken Sapindaceae family fruit seed, and the solvent, wherein a liquid portion remains;
- E. Retiring the solvent from the liquid portion, wherein the liquid portion without the solvent constitutes the material.

In one more aspect of the preparation of the present invention, the mix of broken Sapindaceae family fruit skin and pulp, the unbroken Sapindaceae family fruit seed, and the solvent is exposed to activated carbon before separating all solid particles.

In another aspect of the preparation of the present invention, the Sapindaceae family fruit is the *Sapindus saponaria* fruit.

In one additional aspect of the preparation of the present invention, the solvent amount is at least one part per one part of the total initial weight of the skin plus the pulp plus the seed.

The preparation of the present invention can be used to kill fungi, to kill insects and mites, and also to repel insects and mites.

In addition, the present application invention also provides an extract isolated from *Swinglea glutinosa* leaves, wherein said extract is obtained by a method comprising:
  A. Exposing bright dark green *Swinglea glutinosa* leaves in a dry environment, wherein said leaves are protected from direct sunlight, wherein the leaves are exposed to air flow;
  B. leaving the leaves in the environment described in A. until the leaves turn opaque green and the leaves are brittle;
  C. breaking up the leaves into small fragments;
  D. putting the *Swinglea glutinosa* leaf fragments in contact with a solvent at least once;
  E. repeat step D. until the solvent is enriched with substances derived from the leaf fragments; and,
  F. retiring the solvent to release the extract.

Objectives and advantages of the present application invention will be more evident in the detailed description of the invention and the claims.

DETAILED DESCRIPTION OF THE INVENTION

The present invention provides a method to extract a material from the Sapindaceae family fruit, wherein the method comprises:
  A. Obtaining a Sapindaceae family fruit, wherein the Sapindaceae family fruit is brownish gold, and wherein said Sapindaceae family fruit skin shows wrinkles;
  B. Breaking the Sapindaceae family fruit skin and pulp without breaking the Sapindaceae family fruit seed;
  C. Exposing the broken Sapindaceae family fruit skin and pulp and the unbroken Sapindaceae family fruit seed to a solvent;
  D. Separating all solid particles from the mix of broken Sapindaceae family fruit skin and pulp, the unbroken Sapindaceae family fruit seed, and the solvent, wherein a liquid portion remains;
  E. Retiring the solvent from the liquid portion, wherein the liquid portion without the solvent constitutes the material.

Preferably, in all cases in the present application, where the step of "retiring the solvent from the liquid portion" is mentioned, said step can be performed by evaporating the solvent from the liquid portion. However, "retiring the solvent from the liquid portion" can also be achieved by lyophilization, dry spraying, etc.

In one optional aspect of the method of the present invention, the mix of the broken Sapindaceae family fruit skin and pulp, the unbroken Sapindaceae family fruit seed, and the solvent is exposed to activated carbon before separating all solid particles. However, all solid particles can be separated without exposing the mix of the broken Sapindaceae family fruit skin and pulp, the unbroken Sapindaceae family fruit seed, and the solvent to activated carbon.

For the purpose of this application, the term activated carbon refers to any form of porous carbon with enough surface area for adsorption or chemical reactions. Activated carbon is synonymous to "activated charcoal" or "activated coal".

In another aspect of the method of the present invention, the Sapindaceae family fruit is the *Sapindus saponaria* fruit.

In one more aspect of the method of the present invention, the solvent amount is at least one part per one part of the total initial weight of the skin plus the pulp plus the seed.

The present invention also provides a material derived from a Sapindaceae family fruit, wherein the material is derived from the Sapindaceae family fruit by a method comprising:
  A. Obtaining a Sapindaceae family fruit, wherein the Sapindaceae family fruit is brownish gold, and wherein said Sapindaceae family fruit skin shows wrinkles;
  B. Breaking the Sapindaceae family fruit skin and pulp without breaking the Sapindaceae family fruit seed;
  C. Exposing the broken Sapindaceae family fruit skin and pulp and the unbroken Sapindaceae family fruit seed to a solvent;
  D. Separating all solid particles from the mix of broken Sapindaceae family fruit skin and pulp, the unbroken Sapindaceae family fruit seed, and the solvent, wherein a liquid portion remains;
  E. Retiring the solvent from the liquid portion, wherein the liquid portion without the solvent constitutes the material.

In one aspect of the material of the present invention, the mix of broken Sapindaceae family fruit skin and pulp, the unbroken Sapindaceae family fruit seed, and the solvent is exposed to activated carbon before separating all solid particles. However, all solid particles can be separated without exposing the mix of the broken Sapindaceae family fruit skin and pulp, the unbroken Sapindaceae family fruit seed, and the solvent to activated carbon.

In another aspect of the material of the present invention, the Sapindaceae family fruit is the *Sapindus saponaria* fruit.

In one more aspect of the material of the present invention, the solvent amount is at least one part per one part of the total initial weight of the skin plus the pulp plus the seed.

Furthermore, the present invention provides a preparation that comprises an extract from *Swinglea glutinosa* and a material derived from a Sapindaceae family fruit.

In one main aspect of the preparation of the present invention, the material is derived from the Sapindaceae family fruit by a method comprising:
  A. Obtaining a Sapindaceae family fruit, wherein the Sapindaceae family fruit is brownish gold, and wherein said Sapindaceae family fruit skin shows wrinkles;
  B. Breaking the Sapindaceae family fruit skin and pulp without breaking the Sapindaceae family fruit seed;
  C. Exposing the broken Sapindaceae family fruit skin and pulp and the unbroken Sapindaceae family fruit seed to a solvent;
  D. Separating all solid particles from the mix of broken Sapindaceae family fruit skin and pulp, the unbroken Sapindaceae family fruit seed, and the solvent, wherein a liquid portion remains;
  E. Retiring the solvent from the liquid portion, wherein the liquid portion without the solvent constitutes the material.

In one more optional aspect of the preparation of the present invention, the mix of broken Sapindaceae family fruit skin and pulp, the unbroken Sapindaceae family fruit seed, and the solvent is exposed to activated carbon before separating all solid particles.

For all cases in this application, the material, the method and the preparation, the amount of carbon is one part to one to three parts the amount of the mix. However, the mix of broken the mix of broken Sapindaceae family fruit skin and pulp, the unbroken Sapindaceae family fruit seed, and the solvent, could be evaporated to retire the solvent without exposition to activated carbon.

When the mix is exposed to activated carbon, the resulting material is translucent crystal. When the mix is not exposed to activated carbon the material obtained is turbid and dark. In both cases, the material maintains the surfactant, emulsifying and foaming properties. In either of both cases, the material can be used to be combined with the *Swinglea glutinosa* extract to make the preparation.

In another aspect of the preparation of the present invention, the Sapindaceae family fruit is the *Sapindus saponaria* fruit.

In one additional aspect of the preparation of the present invention, the solvent amount is at least one part per one part of the total initial weight of the skin plus the pulp plus the seed.

The preparation of the present invention can be used to kill fungi, wherein susceptible fungi comprises:
*Sphaerotheca pannosa*
*Botritys* sp.
*Fusarium* sp.
*Colletotrichum* sp.
*Uncinola necator*
*Variola* sp.
*Peronospora* sp.
*Puccinia* sp.
*Cladosporium* sp./*Hetesroporium* sp.,
and others.

For the purpose of the present application the term "to kill fungi" comprises "to prevent fungi".

Moreover, the preparation of the present invention can be used to kill insects and mites, and also to repel insects and mites, wherein susceptible insects and mites comprise:

*Liriomyza* sp
*Tetranichus* sp.
*Boophilus microplus,*
and others.

In addition, the present application invention also provides an extract isolated from *Swinglea glutinosa* leaves, wherein said extract is obtained by a method comprising:

A. Exposing bright dark green *Swinglea glutinosa* leaves in a dry environment, wherein said leaves are protected from direct sunlight, wherein the leaves are exposed to air flow;
B. leaving the leaves in the environment described in A. until the leaves turn opaque green and the leaves are brittle;
C. breaking up the leaves into small fragments;
D. putting the *Swinglea glutinosa* leaf fragments in contact with a solvent at least once;
E. repeat step D. until the solvent is enriched with substances derived from the leaf fragments; and,
F. retiring the solvent to release the extract.

In one more aspect of the *Swinglea glutinosa* extract of the present invention, in the method, the leaves must not be broken into leaf fragments that are less than 0.5 mm, since smaller fragments would tend to become a single mass which will become a limitation for the optimal extraction with a solvent.

In all cases where a solvent is mentioned in this application, the solvent that can be used comprises ethanol, methanol, hexane, propanol, isopropanol, $CO_2$, acetone, water, ethyl-acetate, nitrile-acetate, toluene, tetrahydrofurane, Chloroform, dichloromethane, and others.

In all cases in this application, where solid particles are separated from the mix of broken Sapindaceae family fruit skin and pulp, the unbroken Sapindaceae family fruit seed, and a solvent, the preferred method of separation is centrifugation, although other methods of separation can be used.

The preparation, with the material derived from a Sapindaceae family fruit and the *Swinglea glutinosa* extract of the present invention, can be combined with camphor and oils that have been described to kill fungi, kill and or repel insects and mites, wherein the oils would enhance the effects of the preparation against fungi, insects, and mites, and wherein the oils can be derived from garlic, orange, lemon, lime, *Cymbopogon* sp., *Eugenia caryophyllata, Eucalyptus* sp., *Melaleuca alternifolia, Citrus simensis*, other *citrus* sp., cinnamon, and others.

Objectives and advantages of the present application invention will be more evident in the detailed description of the invention and the claims.

EXAMPLES

Three solutions were prepared: 1) A solution of a 2 ml material/Liter of water (material derived from a Sapindaceae family fruit wherein the material was obtained as described above in this application); 2) A solution of 2 ml extract/Liter of water (extract derived from *Swinglea glutinosa* leaves wherein the extract was obtained as described above in this application) 3) A solution of a 2 ml preparation/Liter of water (preparation made by combining equal parts of the material and the extract). Solutions 1, 2 and 3 were used for the following experiment:

An isolated strain of a pathogenic fungus was propagated in an adequate culture medium for the strain. Then, a suspension on water was prepared at a concentration of $1\times10^6$ spores/ml. Four plates were prepared: one control plate with the culture medium only and three other plates, wherein the three other plates have the cultured medium and 2 ml of each solution. All plates were bathed with 20 μl of the suspension with spores.

After incubation of the plates for 12 days at room temperature the percentage of inhibition for each fungus was measured with the following results:

*Fusarium oxysporum*

| Code | Number of repeats (inhibition %) 1 | 2 | 3 | Average (inhibition %) | Standard Deviation |
|---|---|---|---|---|---|
| SS (material) | 63.4 | 73.2 | 85.2 | 73.9 | 10.9 |
| SW (extract) | 65.9 | 79.8 | 72.5 | 72.7 | 7.0 |
| SW + SS (preparation) | 83.2 | 79.4 | 84.6 | 82.4 | 2.7 |

*Botrytis cinerea*

| Code | Number of repeats (inhibition %) 1 | 2 | 3 | Average (inhibition %) | Standard Deviation |
|---|---|---|---|---|---|
| SS (material) | 39.86 | 38.11 | 52.89 | 43.6 | 8.1 |
| SW (extract) | 76.4 | 85.7 | 79.9 | 80.7 | 4.7 |
| SW + SS (preparation) | 92.3 | 82.1 | 86.7 | 87.0 | 5.1 |

*Mycosphaerella fijiensis*

| | Number of repeats (inhibition %) | | | Average | Standard |
|---|---|---|---|---|---|
| Code | 1 | 2 | 3 | (inhibition %) | Deviation |
| SS (material) | 46.44 | 44.32 | 48.47 | 46.4 | 2.1 |
| SW (extract) | 68.9 | 74.1 | 62.2 | 68.4 | 6.0 |
| SW + SS (preparation) | 75.1 | 84.3 | 81.7 | 80.4 | 4.7 |

*Colletotrichum* sp.

| | Number of repeats (inhibition %) | | | Average | Standard |
|---|---|---|---|---|---|
| Code | 1 | 2 | 3 | (inhibition %) | Deviation |
| SS (material) | 75.66 | 75.47 | 78.82 | 76.7 | 1.9 |
| SW (extract) | 87.5 | 89.9 | 93.2 | 90.2 | 2.9 |
| SW + SS (preparation) | 75.1 | 84.3 | 81.7 | 80.4 | 4.7 |

With respect to *Tetranichus* sp. a repellence test was made by comparing 5 mm discs cut from leaves of bean plants, wherein 5 mm leaf discs that were bathed with 2 ml of each one of the three solutions (solutions 1, 2 and 3) were compared against un-bathed 5 mm leaf discs, and wherein a 2 mm un-bathed leave disc with a *Tetranichus* sp. mites was put on top of all 5 mm leaf discs. The percentage of inhibition (repellence) can be observed in the following results:

*Tetranichus* sp.

| | Number of repeats (inhibition %) | | | Average | Standard |
|---|---|---|---|---|---|
| Code | 1 | 2 | 3 | (inhibition %) | Deviation |
| SS (material) | 56.20 | 52.40 | 49.20 | 52.6 | 3.5 |
| SW (Extract) | 79.3 | 78.8 | 77.2 | 78.4 | 1.1 |
| SW + SS (Preparation) | 82.3 | 89.4 | 84.6 | 85.4 | 3.6 |

With respect to *Liriomyza* sp. a repellence test was made by comparing bathed leaves of bean plants with the 2 ml Extract/Liter of each one of the three solutions (solutions 1, 2 and 3) and un-bathed leaves of bean plants. The plants with bathed and un-bathed leaves were put inside a cage with *Liriomyza* sp. After 24 hours, points of disease caused by *Liriomyza* sp. in plants with bathed and un-bathed leaves were observed. The percentage of inhibition (repellence) in plants with bathed leaves in relation to plants with un-bathed leaves can be observed in the following results:

*Liriomyza* sp.

| | Number of repeats (inhibition %) | | | Average | Standard |
|---|---|---|---|---|---|
| Code | 1 | 2 | 3 | (inhibition %) | Deviation |
| SS (Material) | 38.50 | 41.20 | 45.10 | 41.6 | 3.3 |
| SW (Extract) | 70.4 | 79.2 | 76.2 | 75.3 | 4.5 |
| SW + SS (Preparation) | 78.3 | 84.7 | 87.1 | 83.4 | 4.5 |

For *Sphaerotheca pannosa* a spore suspension was applied to leaves of healthy rose plants bathed with 2 ml of each one of the three solutions (solutions 1, 2 and 3) and to leaves of un-bathed healthy rose plants. Then the leaves of bathed rose plants and un-bathed rose plants were observed for formation of fungi pustules after 15 days. There was between 81.1% and 87.8% less formation of pustules (inhibition) in the leaves of rose plants bathed with the 2 ml the preparation/Liter of water solution, as the following results show:

| | Number of Repeats (inhibition %) | | | Average | Standard |
|---|---|---|---|---|---|
| Code | 1 | 2 | 3 | (inhibition %) | Deviation |
| SS (Material) | 53.1 | 58.5 | 51.6 | 54.4 | 3.6 |
| SW (Extract) | 62.4 | 71.3 | 63.4 | 65.7 | 4.9 |
| SW + SS (Preparation) | 84.6 | 81.1 | 87.8 | 84.5 | 3.4 |

The invention claimed is:

1. A preparation that comprises an extract from *Swinglea glutinosa* and a material derived from a Sapindaceae family fruit, wherein the material is derived from the Sapindaceae family fruit by a method comprising:
   A. Obtaining a Sapindaceae family fruit, wherein the Sapindaceae family fruit is brownish gold, and wherein said Sapindaceae family fruit skin shows wrinkles;
   B. Breaking the Sapindaceae family fruit skin and pulp without breaking the Sapindaceae family fruit seed;
   C. Exposing the broken Sapindaceae family fruit skin and pulp and the unbroken Sapindaceae family fruit seed to a solvent;
   D. Separating all solid particles from the mix of broken Sapindaceae family fruit skin and pulp, the unbroken Sapindaceae family fruit seed, and the solvent, wherein a liquid portion remains;
   E. Retiring the solvent from the liquid portion, wherein the liquid portion without the solvent constitutes the material.

2. The preparation of claim 1, wherein the mix of broken Sapindaceae family fruit skin and pulp, the unbroken Sapindaceae family fruit seed, and the solvent is exposed to activated carbon before separating all solid particles.

3. The preparation of claim 1, wherein the Sapindaceae family fruit is the *Sapindus saponaria* fruit.

4. The preparation of claim 1, wherein the solvent amount is at least one part per one part of the total initial weight of the skin plus the pulp plus the seed.

5. The preparation of claim 1, wherein the preparation is used to kill fungi.

6. The preparation of claim 1, wherein the preparation is used to kill insects and mites.

7. The preparation of claim 1, wherein the preparation is used to repel insects and mites.

\* \* \* \* \*